United States Patent
Brasile (12)

(10) Patent No.: US 6,375,613 B1
(45) Date of Patent: *Apr. 23, 2002

(54) PROGNOSTIC TESTING OF ORGANS INTENDED FOR TRANSPLANTATION

(75) Inventor: Lauren Brasile, Albany, NY (US)

(73) Assignee: Breonics, Inc., Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,952

(22) Filed: Nov. 5, 1999

Related U.S. Application Data

(63) Continuation-in-part of application No. 08/992,284, filed on Dec. 17, 1997, now Pat. No. 6,024,698, which is a division of application No. 08/670,569, filed on Jun. 26, 1996, now Pat. No. 5,699,793, which is a continuation-in-part of application No. 08/246,801, filed on May 20, 1994, now abandoned.

(51) Int. Cl.$^7$ ................................................. A61B 5/00
(52) U.S. Cl. ........................................ 600/300; 600/309
(58) Field of Search ........................ 600/30 T; 514/60; 435/15, 1.1

(56) References Cited

U.S. PATENT DOCUMENTS

| | | | |
|---|---|---|---|
| 4,798,824 A | * | 1/1989 | Belzer et al. .................. 514/60 |
| 5,552,267 A | * | 9/1996 | Stern et al. ................... 435/1.1 |
| 5,635,365 A | * | 6/1997 | Ansari et al. .................. 435/15 |
| 5,699,793 A | * | 12/1997 | Brasile ........................ 600/300 |

* cited by examiner

Primary Examiner—Eric F. Winakur
(74) Attorney, Agent, or Firm—Heslin Rothenberg Farley & Mesiti P.C.

(57) ABSTRACT

The present invention discloses a method of prospectively determining whether an organ will function once it is transplanted. A transplantable organ is perfused in an ex vivo warm perfusion system capable of supporting near normal levels of metabolism by the organ. One or more parameters related to organ function are measured and evaluated during perfusion. Measurements of perfused organ function are compared to values indicative of normal organ function to obtain a prediction of whether the organ being perfused will function once it has been transplanted. A method for calculating a viability index based on the parameters evaluated is also disclosed.

26 Claims, 2 Drawing Sheets

PROGNOSTIC TESTING OF ORGANS INTENDED FOR TRANSPLANTATION

CROSS-REFERENCE TO RELATED APPLICATIONS

This application is a continuation-in-part of U.S. patent application Ser. No. 08/992,284, filed Dec. 17, 1997 now issued as U.S. Pat. No. 6,024,698 which is a division of U.S. patent application Ser. No. 08/670,569 filed Jun. 26, 1996, now issued as U.S. Pat. No. 5,699,793, which is a continuation-in-part of U.S. patent application Ser. No. 08/246,801 filed May 20, 1994, now abandoned; the disclosures of these applications are incorporated herein by reference in their entirety.

FIELD OF THE INVENTION

The invention relates to a method of prospectively evaluating organ function while the organ, which is intended for transplantation, is being maintained at a near normal rate of metabolism. More particularly, the method involves measuring one or more indicia of organ function, as a means of assessing functional capabilities of the organ which can then be correlated with its posttransplantation course.

BACKGROUND OF THE INVENTION

Transplantation is the therapy of choice for people with end-stage organ failure. In the case of end-stage heart, liver and lung disease, transplantation is the only life-saving therapy. The major limiting factor today in clinical transplantation is the persistent shortage of organs. For example, of the 265,000 patients with end-stage kidney disease in the U.S., only 5–6% will ever receive a transplant. World-wide there are more than 460,000 patients with end-stage kidney disease alone. Recent estimates indicate that approximately 30% of the End Stage Renal Disease (ESRD) population could benefit from a transplant if kidneys were available.

The patients who are considered for organ donation are primarily heart-beating cadaver donors (HBD), patients with head trauma who are maintained on a respirator in an intensive care unit prior to declaring death by brain criteria. Since these brain dead patients are maintained on a respirator until the time of organ donation, the organs rarely experience substantial warm ischemic (WI) damage. Unfortunately, HBD represent a very small perecentage of the patient population that expire each year from a traumatic injury. The HBD represents a limited supply of organs for transplantation that has remained constant for the past ten years.

There have been recent attempts to expand the organ donor pool for transplantation by using marginal organs, i.e. organs procured from elderly donors or those that have been hypothermically preserved for extended periods of time (>24 hrs). But these sources of marginal donors represent a modest expansion of the donor pool at best. Organs from non-heartbeating donors (NHB) are not commonly used in organ transplantation because the time period between cardiac arrest and intervention represents a threshold of damage from WI injury (<1 hour) that makes the posttransplantation outcomes uncertain. The major reason why the organ donor pool cannot be expanded into this substantially larger pool of non-heartbeating donors is that currently there is no ex vivo test available to measure the extent of the WI damage and/or predict which organs will function and which will not after they are transplanted. In kidneys from NHB the immediate non-function rate is >80%. This significantly decreases the cost effectiveness of the transplant when prolonged postoperative dialysis must be applied. In the case of hearts and livers, where immediate function is necessary, organs procured from marginal and NHB donors are not considered.

A much larger, untapped pool of patients consists of the non-retrievable donor (NRD), i.e. the patient in whom circulatory arrest has existed for >1 hour postmortem without any intervention and which represents the vast majority of patients dying each year from a traumatic injury. These NRD are never considered for organ donation.

Current organ preservation technology depends upon the use of hypothermia by either continuous hypothermic perfusion or simple hypothermic storage (see, for example, Collins et al., 1969, Lancet 2:1219). While a variety of perfusates have been utilized clinically, these two methods of organ storage have remained substantially unchanged for the past 20 years. The current perfusate solution that represents the state-of-the-art in hypothermic organ preservation, and that provides for optimized organ preservation under hypothermic conditions, contains components that prevent hypothermia-induced tissue edema; metabolites that facilitate organ function upon transplantation; antioxidants; membrane stabilizers; colloids; ions; and salts (Southard et al., 1990, Transpl. Proc., 21:1195). The formulation of this perfusate is designed to preserve the organs by hypothermia-induced depression of metabolism. While it minimizes the edema and vasospasm normally encountered during hypothermic storage, it does not provide for a substantially expanded donor pool because, at the temperatures used in hypothermic organ preservation (4°–8° C.), metabolism is suppressed by more than 95%. With virtually no metabolism, it is not possible to prospectively evaluate which organs will function once transplanted.

Recent efforts are in progress utilizing materials and techniques to resuscitate and repair ischemically damaged tissues and organs (U.S. Pat. No. 5,843,024). These techniques support organ resuscitation and preservation by supporting ongoing metabolism. Metabolism by the organ is sufficiently supported so that the organ continues to function during the period of ex vivo preservation. Because organ metabolism and function are ongoing, the potential exists for establishing parameters based on the function of the organ during ex vivo perfusion that can be applied to predict how the organ will function when it has been transplanted. Developing the ability to predict if an organ will function upon transplantation would provide a basis for expanding the donor pool.

The ability to expand the organ donor pool using this technology will be dependent upon the ability to differentiate those organs that represent reversible injury, commonly referred to as delayed graft function (DGF), or, in the case of kidneys, acute tubular necrosis (ATN), from those with irreversible injury, referred to as primary nonfunction (PNF). Currently, in clinical transplantation, there is no validated methodology to evaluate organ function prospectively. The result of having to transplant an organ without knowledge of its functional status is a very narrow definition of donor suitability that contributes to the continuing organ shortage.

One of skill in the transplantation art will recognize, therefore, that an important goal in any attempt to expand the existing organ donor pool is the development of a successful diagnostic tool having the ability to differentiate reversible damage (DGF or ATN) from irreversible damage (PNF) in an allograft. A successful prognostic test would have to prospectively evaluate the functional capacity of an allograft with a high degree of confidence.

SUMMARY OF THE INVENTION

In one aspect, the invention relates to a method for prospectively determining the functional potential an organ to be transplanted. According to the method, one obtains a value by measuring a parameter related to organ function of a fluid derived from an explanted organ selected from organ product, circulated perfusate, and a combination thereof, comparing the value obtained with a range of reference values indicative of normal organ function; and determining whether or not the value obtained falls within the range of reference values indicative of normal organ function.

In another aspect, the invention relates to a method for prospectively determining the functional potential of an organ to be transplanted, while the organ is being perfused in a warm preservation system, which allows for near normal levels of metabolism by the organ. According to the method, one evaluates one or more of the following parameters alone or in combination: normalization of perfusion characteristics for the organ, the extent of damage to the vascular endothelium of the organ, the level of oxidative capacity of the organ, and the metabolic capacity of the organ.

In a related aspect, the invention relates to a method for prospectively determining the functional potential of a kidney to be transplanted, by additionally evaluating one or more of the following parameters: the extent of leakage of a perfusate protein into urine produced by the kidney, the ability of the kidney to reabsorb ions, the ability of the kidney to secrete ions, and the ability of the kidney to retain a tracer molecule, such as an intracellular enzyme.

In still another aspect, the present invention relates to a method for prospectively determining the functional potential of a liver to be transplanted, by additionally evaluating one or more of the following parameters: rate of bile flow from the liver; concentration of liver enzymes in bile; concentration of bile salts; osmolarity of bile; bile pH; and bile color.

In yet another aspect, the present invention relates to a method for prospectively determining the functional potential of a pancreas to be transplanted, by additionally evaluating one or more of the following parameters: the pancreas; lipase activity of the pancreas; and insulin production by the pancreas.

In still another aspect, the present invention relates to a method for prospectively determining the functional potential of a heart to be transplanted, by additionally evaluating one or more of the following parameters: mechanical activity of the heart; electrical activity of the heart; and production of heart enzymes.

In still another aspect, the present invention relates to a method for prospectively determining the functional potential of a small bowel to be transplanted, by additionally evaluating one or more of the following parameters: production of gastric secretions from the small bowel; concentration of gastric secretions from the small bowel; pH of gastric secretions from the small bowel; and ability of the small bowel to absorb tracer molecules.

In still another aspect, the present invention relates to a method for prospectively determining the functional potential of an organ to be transplanted, by calculating a viability index. According to the method, a value is assigned to each of the parameters evaluated; the viability index is the sum of these values and is indicative of potential function of the organ once it has been transplanted.

In a related aspect, the invention relates to a method for determining the extent of damage to the vascular endothelium of a transplantable organ by assessing one or more of the following: the degree of platelet activation, the degree of platelet adherence to or the degree of platelet release from the vascular tissue of the organ.

In a related aspect, the invention relates to a method for determining the severity of ischemic damage of an organ intended for transplant, wherein the organ is being perfused in a warm preservation system allowing for near normal levels of metabolism by the organ. According to the method, one evaluates one or more of the following parameters alone or in combination: normalization of a perfusion characteristic for the organ, the extent of damage to the vascular endothelium of the organ, the level of oxidative capacity of the organ, and the metabolic capacity of the organ. Optionally, the method provides for calculating a viability index, which is the sum of values for each of the measured parameters. The viability index is indicative of the severity of ischemic damage in the organ.

In a related aspect, the present invention relates to a method for prospectively identifying primary non-function (PNF) in an organ intended for transplant. According to the method, one measures one or more of the following parameters alone or in combination: normalization of a perfusion characteristic for the organ; extent of damage to the vascular endothelium of the organ; level of oxidative capacity of the organ; and metabolic capacity of the organ. It is then possible to determine the functional potential of the organ being perfused by comparing the measurement obtained for the organ being perfused with a measurement indicative of normal organ function.

Figure 1:
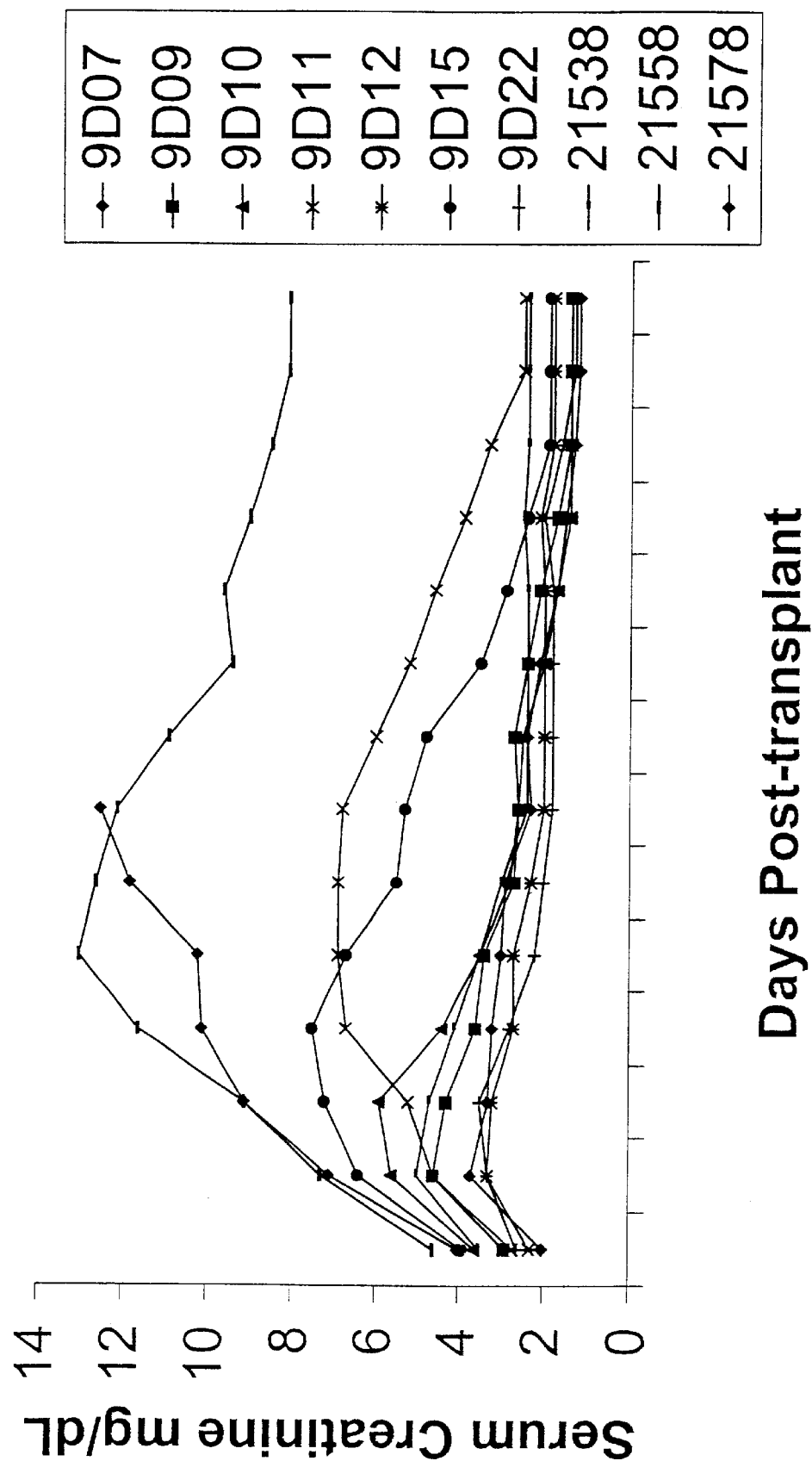
FIG. 1 represents serum creatinine levels on various days posttransplantation in nine test animals.

All patents, applications, publications, or other references that are listed herein are hereby incorporated by reference.

In the description that follows certain conventions will be followed as regards the usage of terminology: the term "transplantable organ" refers to any organ or tissue which is harvested from a donor and intended to be transplanted into a recipient, including, but not limited to kidney, heart, liver, lung, small bowel, pancreas, and eye.

The term "warm temperature perfusion," "warm perfusion" or "perfused in a warm preservation system" refers to perfusion of the organ at a temperature in the range of about 16° C. to about 38° C., with a perfusate composed of a highly enriched and modified tissue culture medium which provides necessary oxygen delivery, nutrients for metabolism, oncotic pressure, pH, perfusion pressures, and flow rates to support organ metabolism ex vivo within or near the normal range of metabolism in vivo.

The term "near normal levels of metabolism" or "near the normal range of metabolism" is defined as about 50–100% of the normal rate of metabolism for a particular organ as determined by measuring and evaluating whether functional characteristics of an organ such as those described in U.S. Pat. No. 5,699,793, are within the range associated with normal function for that particular organ. Examples of functional characteristics include, but are not limited to, electrical activity in a heart as measured by electrocardiogram; physical and chemical parameters of organ product, for example, oxygen consumption and glucose utilization, which can be ascertained from perfusate concentrations; pancreatic enzymes; heart enzymes; creatinine clearance and specific gravity of urine and so on.

The terms "perfusion solution" and "perfusate" are used interchangably and refer to a blood-free buffered physiologic solution. Preferred perfusion solutions provide means for reestablishing cellular integrity and function in organs which may have experienced ischemic or other damage prior to or during isolation and further, enable an organ or tissue to be maintained at a near normal rate of metabolism.

The term "metabolic capacity of an organ" refers to the organ's oxidative and anaerobic metabolic capabilities.

The term "exocrine production" refers to production of an organ product which is secreted outwardly from the organ, usually by means of a duct, for example, pancreatic secretions. Similarly, the term "exocrine concentration" refers to the concentration of constituents of the organ product generated by an exocrine organ.

For purposes of practicing the invention, normal values and ranges for chemical and physical parameters of organ product, and other measurements indicative of normal organ function are those values referenced in textbooks known to those of skill in the medical arts on physiology and clinical chemistry, plus or minus 20%. See *CRC Handbook of Clinical Chemistry*, Mario Werner, editor, CRC Press; Stuart Ira Fox *Human Physiology*, 6th edition, William C. Brown, publisher.

The method of the present invention provides for a prospective evaluation, that is, before it is ever transplanted, of a transplantable organ's functional potential. Prior to transplantation, a transplantable organ is perfused in a warm preservation system such as the exsanguinous metabolic support (EMS) system described in U.S. patent application Serial No. 60/129,257, the contents of which are incorporated herein by reference in its entirety. During the time that it is being perfused, various parameters relating to the functional and metabolic capabilities of the organ are monitored. Based on the information obtained regarding these capabilities, the degree of reversible or irreversible injury sustained by the organ can be assessed and a determination of the likelihood that the organ will function after it has been transplanted can be made.

Briefly, the organ is flushed with a perfusion solution, such as that described in U.S. Pat. No. 5,843,024 to remove blood and acidotic products. Subsequently, the organ is perfused at a temperature in the range of about 16° C. to about 38° C., preferably 25° C. to 32° C., with a perfusion solution which provides the necessary oxygen delivery, nutrients for metabolism, oncotic pressure, pH, perfusion pressures, and flow rates to support organ metabolism ex vivo within or near the normal range of metabolism in vivo. Further, the warm preservation system supports a level of metabolism which provides enough oxidative metabolism to result in the normal functional product of the organ.

During perfusion, various parameters of the perfusion and of the perfusion solution are monitored. These parameters are related to the perfused organ's functional and metabolic capabilities. The present invention provides a method for predicting transplant outcomes, utilizing information regarding the ongoing metabolism of the organ during warm temperature perfusion of the organ. The parameters used for organ evaluation include, but are not limited to: innate metabolic potential; initial and overall oxygen consumption by the organ; ability of the organ to normalize the perfusion pressures and flow rate; estimation of the vascular integrity of the organ and normal production of organ product. In specific organ types, other parameters of organ metabolism and function may be relevant. For example, where the organ is a kidney, additional parameters include leakage of perfusate protein into the urine, the ability of the kidney to reabsorb $Na^+$, $Cl^-$, and $Mg^{++}$, secrete $K^+$, or retain an intracellular enzyme, such as, lactate dehydrogenase (LDH), gamma glutamyl transferase (GGT), and aspartate transaminase (AST). In the liver, additional parameters include: rate of bile flow from the liver; concentration of liver enzymes in bile; concentration of bile salts; osmolarity of bile; bile pH; and bile color. Where the organ to be transplanted is a pancreas, additional parameters include: exocrine production by the pancreas; exocrine concentration; amylase activity of the pancreas; lipase activity of the pancreas; and insulin production by the pancreas. Functional characteristics of small bowel include: production of gastric secretions from the small bowel; concentration of gastric secretions from the small bowel; pH of gastric secretions from the small bowel; and the ability of the small bowel to absorb tracer molecules. Where the organ to be transplanted is a heart, additional parameters include: mechanical activity of the heart; electrical activity of the heart; and production of heart enzymes.

Evaluation of Metabolic Capacity

Prior to establishing an organ in a warm perfusion system, the organ is flushed with an amount of the perfusion solution sufficient to remove accumulated blood and acidotic products formed as the result of blood flow deprivation, approximately 150 ml. Evaluation of the $O_2$, $CO_2$ and pH of the flush solution provides information regarding the organ's innate metabolic capacity. Measurements of the partial pressures of $O_2$ and $CO_2$, and pH of the perfusion solution are taken before and after flushing of the organ. Uptake of $O_2$ by the organ, normalized for organ size is equivalent to the change in oxygen tension in the perfusion solution divided by the weight of the organ:

$$\frac{O_2 \text{ pre-flush (mmHg)} - O_2 \text{ post-flush (mmHg)}}{gm}.$$

Similarly, an increase in $CO_2$ in the perfusion solution as a result of the flush is given by:

$$\frac{CO_2 \text{ pre-flush (mmHg)} - CO_2 \text{ post-flush (mmHg)}}{gm}.$$

The change in pH units is also normalized for organ weight:

$$\frac{pH \text{ pre-flush} - pH \text{ post-flush}}{gm}.$$

In one embodiment of the present invention, an index of metabolic capacity is calculated as:

$$\frac{O_2 \text{ uptake by the organ}}{\text{the change in } CO_2 \div \text{the change in pH}}.$$

Thus, the ratio of oxygen uptake by an organ to the $CO_2$/pH index during the transition from cold storage to temperatures suitable for warm perfusion provides a preliminary assessment of the anaerobic metabolic capacity following ischemia and cold preservation. The calculated ratio correlates with outcomes in that organs with the highest ratios have a high probability of function following allograft. Similarly, organs with the lowest ratios have poorer outcomes. Where the organ is a kidney, the $O_2/CO_2$-pH ratio correlates with reversible damage in that organs having the shortest periods of ATN have the highest $O_2/CO_2$-pH ratios.

Evaluation of Oxidative Capacity

One parameter by which to prospectively determine an organ's functional potential once it has been transplanted is to evaluate its oxidative capacity, that is, its ability to reestablish oxidative metabolism once a source of $O_2$ is provided. With respect to an organ's oxidative capacity, the organ's initial oxygen consumption ($O_{2i}$) during warm perfusion compared to its mean stabilized consumption ($O_{2s}$) provides an estimate of the degree of impairment of the organ.

In one embodiment of the invention, therefore, $O_2$ consumption of the perfused organ is measured within the first fifteen minutes of perfusion. The amount of oxygen consumption for a transplantable organ undergoing warm temperature perfusion is calculated as follows:

$$\text{Oxygen Consumption (cc/min/gm)} = \frac{(\text{Arterial PaO}_2 - \text{Venous PaO}_2) \times (\text{Flow Rate})}{\text{Weight}}$$

Values are then obtained for at least one other selected time interval, for example, one, two and three hours after initiation of perfusion, and a mean value obtained for the organ's stabilized consumption rate. An oxidative index, which is the ratio of initial $O_2$ consumption ($O_{2i}$) to stabilized $O_2$ consumption ($O_{2s}$) is indicative of the extent of impaired oxidative metabolism. For example, in the kidney, those organs that have substantially reduced rates of oxygen consumption at the start of warm perfusion experience longer periods of ATN. Thus, as evidenced by the data in Table 1 below, an oxidative index ($O_{2i}/O_{2s}$) close to 1.0 is indicative of mild ATN. An oxidative index below 0.9 indicates moderate ATN while oxidative index values below 0.5 indicate severe ATN or PNF. In the study described below, one kidney in which the initial oxygen consumption was severely impaired (oxidative index=0.33), represented the upper limit of ATN in this model with a peak serum creatinine of 13.0 mg/dL on day 5 (kidney #9)(Table I). Another with severely impaired initial oxygen consumption (oxidative index=0.30) proved to be PNF (kidney #10) (Table I).

Normalization of Perfusion Parameters

Another parameter by which to prospectively determine an organ's functional potential prior to transplantation is to evaluate, during perfusion, its ability to normalize parameters of the perfusion. Normal perfusion pressures are, generally, in the range of 20 mmHg to 90 mmHg, while normal flow rates are between 80 and 400 cc/min. For example, the ability of a kidney to regain normal perfusion pressures of about 40–90 mmHg and flow rates of about 80–150 cc/min, is indicative of reversible damage. In the case of heart, normal perfusion pressures for a heart are in the range of about 30–60 mmHg and flow rates are in the range of 80–400 cc/min. A normal organ, that is, one which has not suffered any injury as the result of warm ischemia or cold preservation, will normalize vascular pressures and flow rates immediately when perfused. Organs with reversible damage will normalize within 3 hours. Those with irreversible damage will not normalize within three hours.

In the studies described below, the only kidney that did not regain normalized perfusion during the period of warm perfusion was the only kidney with PNF (Table I). In one embodiment of the present invention, where a viability index based on various criteria is calculated, a score, for example, +1, is assigned to those organs in which normal perfusion characteristics are achieved during the perfusion period. If the perfusion characteristics remain out of the normal range, a score of −1 is assigned.

Evaluation of Vascular Integrity

Loss of vascular integrity in an organ intended for transplant reduces the likelihood that the organ will function normally after it has been transplanted. Thus, a good prognostic indicator of an organ's ability to regain its functional potential after it has been transplanted is an evaluation before transplant of the vascular integrity of the organ. One method for assessing the extent of damage to the vascular compartment of a transplantable organ is by measuring the degree of platelet activation in the organ. This may be accomplished by performing on the perfusate or platelets found in the perfusate, various tests which evaluate platelet activation, including but not limited to: release of platelet activating factor (PAF); detection of expressed adherence molecules on the surface of the platelets found in the perfusate; measurement of CD40L (CD154) expression of platelets in the perfusate; release of von Willebrand factor from vascular endothelium of the organ; measurement of upregulation or activation of fibrinogen receptor, GPIIb/IIIa; platelet secretions or degranulization; platelet serotonin receptor (5HT2A) density; upregulation of CD42; amount of thromboxane B2; measurement of platelet accessory cell function, for example, modulation of monocyte chemotactic protein 1 (MCP-1); upregulation of ICAM-1 in vascular endothelium; evaluation of adhesive cell receptors such as GPIb-α, GPIV, P-selectin, platelet-endothelial cell adhesion molecule PECAM-1; CD62 or CD63 activation of antigen expression in platelets and the like.

Similarly, the extent of platelet adherence to the vasculature or release of platelets from the organ are indicia of vascular injury. Generally, a decrease in platelet number is associated with thrombosis, while an increasing platelet count during perfusion indicates damage resulting in edema and constriction which prevent adequate flushing and preservation of the vasculature. In one embodiment of the present invention, platelet counts are obtained at the initiation of warm perfusion and are monitored over the course of warm perfusion. By comparing the initial platelet concentration of the perfusate to the platelet concentration after a period of perfusion, for example, two hours, an overall assessment of the extent of vascular damage can be approximated. A value can be assigned which can then be used in combination with other parameters to calculate a viability index. For example, a negative (−) 1 is assigned to organs in which the platelet number during perfusion is less than the initial value. This is indicative of platelet adherence within the organ. Where the number of platelets increases during perfusion, a value is assigned which represents the total increase of platelets. For example:

1.0 represents an increase of 0 to 1,000 platelets;
0.85 represents an increase of 1,000 to 2,000 platelets;
0.75 represents an increase of 2,000 to 3,000 platelets;
0.50 represents an increase of 3,000 to 4,000 platelets;
0.25 represents an increase of 4,000 to 6,000 platelets;
0.15 represents a increase of greater than 6,000 platelets;

As demonstrated by Table I, using a scoring system like this one, a score of 1 is an indication that there is little loss of vascular integrity, while a score of 0.15 correlates with PNF.

The parameters described above may be employed singly or in combination in the method of the present invention to evaluate the functional potential of any transplantable organ prior to transplantation. Although a single parameter may be used to predict functional potential of an organ, the use of multiple parameters improves the precision of the prediction. Depending on the organ being evaluated, additional parameters which are indicative of the functional potential of a specific type of organ may be employed. For example, the functional potential of a pancreas can be assessed using methods known to one of skill in the art to measure parameters including, but not limited to: exocrine production by the pancreas; concentration and enzymatic activity of pancreatic enzymes such as amylase and lipase; concentration of other constituents of the pancreatic secretion; insulin production; sodium and potassium concentrations and pH of the pancreatic secretion.

In the kidney, glomerular function is another parameter which may be evaluated in accordance with the method of the present invention. Glomerular function during the period of perfusion may be assessed by determining whether and to what extent there is leakage of a perfusion protein or other tracer molecule into the urine produced by the kidney. Suitable tracer molecules include molecules having a molecular weight in the range of 30,000–180,000 daltons, or preferably, in the range of 50,000–150,000. Examples include but are not limited to: perfluorochemical emulsions, dextran, inulin, immunoglobulin, albumin and the like. The appearance of tracer molecules in the urine produced by a perfused kidney indicates that there has been some loss of glomerular function in the kidney.

Where the functional potential of a liver is to be assessed, it may be desirable to evaluate bile production, concentration of liver enzymes in the bile; concentration of bile salts; osmolartiy, pH and color of the bile produced.

Functional characteristics of a heart include the mechanical activity of the heart; electrical activity of the heart as measured by electrocardiogram (ECG), and production of heart enzymes, for example transaminases, such as aspartate aminotransferase, (AST), lactate dehydrogenase (LDH), fructose 1,6-diphosphate aldolase (ALS), malate dehydrogenase (MD), glutathione reductase (GR), creatine phosphokinase (CPK), hydroxybutyrate dehydrogenase (HBD),. Indicators of cardiocascular disease may include increased levels of AST, LDH,ALS, MD, GR, CPK and HBD.

Viability Index

A viability index, based on the indicia of organ function outlined above, may be used in the method of the present invention to identify and classify the severity of ischemic damage in a transplantable organ, thereby providing a means to grade reversible injury and identify potentially useful organs. For example, in the study detailed below, kidneys were evaluated with respect to the following parameters: metabolic capacity; oxidative capacity; vascular integrity and ability to normalize perfusion characteristics. A value was assigned to each parameter as described above. The sum of these values provides a viability index indicative of the functional potential for the organ being evaluated. The range of values obtained are predictive of the degree of ATN in kidneys, for example, mild, moderate or severe. In addition, the viability index is able to predict cases of irreversible damage, enabling damaged organs to be eliminated from the potential donor pool. Therefore, the viability index provides for a sensitive test that can be used to evaluate an organ prospectively.

To evaluate the feasibility of the method of the present invention to provide a prognostic indication of success or failure of transplantation of an organ, the following study was performed. The study employed a canine autotransplantation model standardized over the past ten years at the University Hospital Center in Maastricht, The Netherlands. The model consisted of an initial insult of 30 minutes of warm ischemia by mobilizing the kidney and leaving the excised kidney in the peritoneum for the duration of the warm ischemic period. Subsequent to the warm ischemic insult, the kidney was flushed and statically stored in ViaSpan™ at 4° C. for 24 hours. In previous studies using this model, when the kidney is directly transplanted from the cold, approximately 70% of the transplanted kidneys eventually regain function, while 30% succumb to PNF.

In this study, the kidneys were transitioned to the near physiologic temperature perfusion conditions of the warm perfusion system for three hours prior to reimplantation. During the period of warm perfusion, renal metabolism and function were quantified. Indicative parameters were identified and successfully employed to predict outcomes prospectively. Additionally, a viability index is described that includes calculations for innate metabolic capacity, perfusion characteristics, oxidative metabolism and the condition and barrier function of the vasculature.

Animals

Mixed fox hounds were used for this study. The canines were conditioned and blood work was performed prior to use. All canines demonstrated normal renal function prior to the start of the study. The ten canines utilized in this study were followed during the posttransplant period and outcomes determined by serum chemistries, urinalysis and histopathologic determinations. The control group used consisted of seven historic controls and four canine transplantations performed just prior to the test experiments.

The excised kidneys were exposed to 30 minutes of warm ischemia while remaining in the abdominal cavity (37° C.). Following the warm ischemic period, the kidneys were flushed with approximately 200 cc of ViaSpan at 4° C. The kidney was then statically stored in the ViaSpan in packed ice for approximately 24 hours.

EMS Perfusion

Following the period of cold ischemia, the kidneys were temperature transitioned by flushing with EMS solution warmed to 32° C. The warmed kidneys were then placed on EMS perfusion for approximately 3 hours. During the 3 hour EMS perfusion, aliquots of the perfusate and any urine produced were taken for laboratory testing of oxygen consumption, glucose, alkaline phosphatase, gamma glutamyl transferase (GGT), LDH, total protein, electrolytes, albumin and BUN.

The contralateral kidneys were nephrectomized. The EMS perfused kidneys were then autotransplanted using an end-to-side anastomosis made between the renal artery and the aorta, and the renal vein to the vena cava.

The bladder was mobilized and a 2-cm incision made through the first and second layers and the mucosa of the bladder. The muscle was tunneled over the ureter, with the ureter being anchored to the bladder with suture. Following transplantation the canine was closed and allowed to recover.

Each day the serum creatinine and BUN values were posted to determine the clinical course. Continued survival was decided by the clinical evaluation provided by the attending veterinarian. One animal deemed to be in poor condition, with unlikely chance of recovery from the ATN was classified as primary nonfunction (PNF). The transplanted kidney was excised and fixed for histologic evaluation. Those canines tolerating the ATN clinically and demonstrating normalizing trends in serum creatinine and BUN values were maintained until the serum chemistries were normalized or, if the values remained elevated, until the serum creatinine and BUN values stabilized. At the time of euthanasia, all kidneys were excised, fixed and histologically evaluated.

Upon completion of the study, the laboratory, histologic and clinical data were compared to the outcomes to identify any significant prognostic potential of the metabolic and functional parameters.

The results are as follows: kidneys with the shortest period of and least severe ATN (1) produced urine during warm perfusion, (2) did not leak protein, (3) were capable of reabsorbing Na+, Cl-, and Mg++, and (4) were capable of secreting potassium.

All ten test kidneys reperfused well with instantaneous reperfusion and normal turgor. Many of these kidneys produced urine within minutes of reperfusion. In nine of the transplantations, the kidneys produced urine within the first four hours of reimplantation. In these same nine transplants, the next morning the serum creatinine values ranged from 2.3–4.6 mg/dL, with a mean value of 3.3 mg/dL (FIG. 1). The serum creatinine values continued to rise with peak creatinine values occurring on posttransplant day 2–5, for the nine dogs with the mean peak serum creatinine occurring on day 2.9. In the nine dogs with a reversible period of ATN, the serum chemistries were normalized on posttransplant day 6–11, with a mean period of ATN of 8.8 days (FIG. 1).

The creatinine concentration in the first urine produced postoperatively ranged from 2.4–7.5 mg/dL, with a mean value of 4.9 mg/dL. In the nine dogs with reversible damage the urinary creatinine concentrations rapidly increased over subsequent days with normalization several days prior to the normalization of the serum chemistries.

In the tenth dog the serum creatinine value continued to rise with corresponding uremia and diminished urine output. On the seventh posttransplant day the dog was euthanized with serum creatinine value of 12.5 mg/dL (FIG. 1). Similar to the dogs with reversible ATN, this dog also demonstrated an increasing urinary creatinine concentration that was 20.0 mg/dL by 48 hours posttransplant. Although this dog did not tolerate the uremia, the urinary creatinine concentration continued to rise, with a value of 48.3 mg/dL on the day the dog was euthanized.

Figure 2:
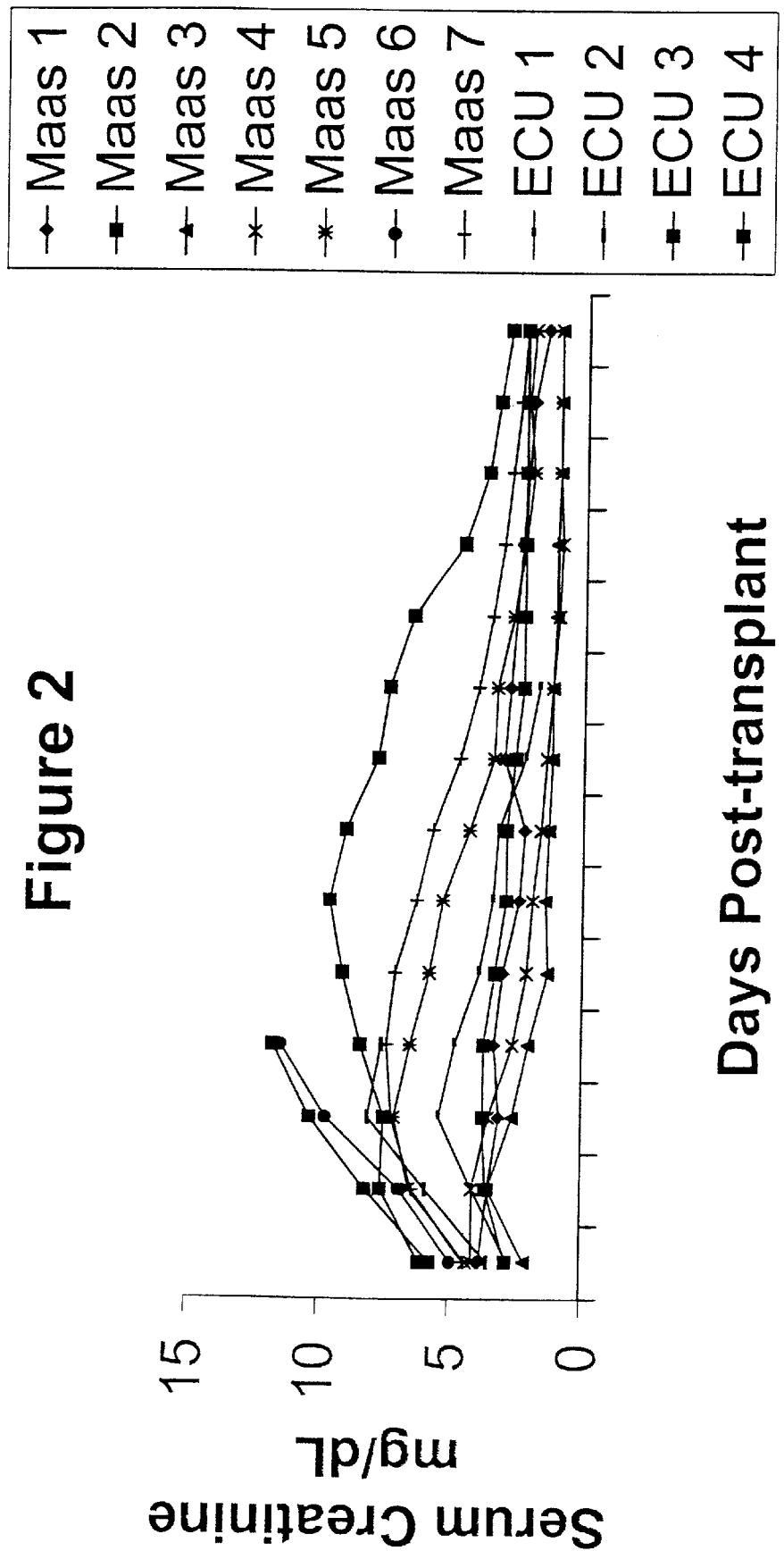
FIG. 2 represents serum creatinine levels on various days posttransplantation in 11 control animals.

None of the control kidneys produced urine on the operating table nor during the first hours posttransplant. At 24 hours posttransplant the serum creatinine values ranged from 2.1–6.1 mg/dL, with a mean serum creatinine value of 4.0 mg/dL (FIG. 2). Recovery from the ATN occurred in 8/11(73%) of the control dogs. However, in several of these control dogs with reversible damage, the serum chemistries never fully normalized.

Histology

The kidney specimens were fixed in 10% neutral buffered formalin and sectioned in standard fashion. The kidney sections were processed, cut into 4 micron sections and stained with H&E using standard histologic methods. Evaluations of the kidney sections were conducted using standard light microscopic techniques.

In the nine dogs exhibiting a reversible ATN with normalization of the serum chemistries, the histologic evaluation of the kidney sections provided evidence of widespread, intermittent cystic dilation of tubules with flattened or regenerating tubular epithelium. There was mild, multifocal mineralization of the cortical tubules. Mild inflammatory infiltrates were found to be associated with areas of regeneration, repair and mineralization. The blood vessels appeared to be normal. There was some incidence of an occasional proliferative glomerulonephritis with neutrophils.

In the tenth dog with PNF, the kidney sections revealed a markedly different histologic evaluation. There was moderate, segmental, acute glormerulonephritis with glomerular thrombosis, neutrophil infiltrates and occasional mesangial proliferation. There was also marked interstitial hemorrhage and tubular necrosis. Several wedge-shaped hemorrhagic infarcts extending from the medulla were observed. The infarcts were interspersed with areas of ATN. Other areas were characterized by severe medullary hemorrhagic necrosis with marked infiltration of neutrophils. Focal arteriolar thrombosis was also observed.

The kidney sections from control dogs that eventually recovered normalized serum chemistries displayed histology similar to that of the nine test dogs with full recovery of renal function. The histologic evaluation revealed regenerating tubules, normal blood vessels and the occasional occurrence of proliferative glomerulonephritis In the study described above, a viability index was calculated as the sum of each of four parameters: metabolic capacity, oxidative capacity, vascular integrity and normalization of perfusion characteristics, i.e. vascular flow rate and perfusion pressure. Those dogs experiencing the least severe ATN in terms of the peak serum creatinine values, and also having the shortest time to normalization of the serum chemistries, were also found to have (Table 1) the highest viability index ( dogs # 1, 2 & 3). Classified as having a mild ATN, the mean peak serum creatinine value was 3.5 mg/dL and the mean time to normalization of the serum chemistries was 7.5 days in these three dogs. Therefore, in this instance, a viability index in the range of 2.5 to 2.9 was found to be associated with mild ATN. Similarly, a viability index in the range of 2.2 to 2.45 was found to be associated with a moderate ATN. The dogs having a viability index in this moderate range experienced a period of ATN with a mean peak serum creatinine value of 5.6 mg/dL and the mean time to normalization of the serum chemistries was 10.5 days (dogs #4, 5 , 6, & 7) (Table I). When the calculated viability index was found to be in the range of 1.5 to 2.00, the ATN was observed to be severe. In the two dogs experiencing a severe ATN, the mean peak serum creatinine value was 10.3 mg/dL and the mean time to normalization of the serum chemistries was 19 days (dogs #8 &9) (Table I). Therefore, there appeared to be a direct correlation between a decreasing viability index and an increase in the severity of the ATN, both in terms of the peak serum creatinine and time necessary for repair.

In dog #10 (Table I) the calculated viability index was negative. The posttransplant course in this dog revealed rising serum creatinine and BUN values that did not peak. The dog was symptomatic of uremia and was euthanized on day 7 posttransplant with a serum creatinine of 12.5 mg/dL. Dog #10 was designated as the one case of PNF in this study.

It should be understood that the embodiments and the examples of the present invention, as described herein, are for purposes of illustration only, and not limitation, and any changes, modifications or additions as will become apparent to one of ordinary skill in the art from the foregoing description and accompanying figures are intended to be included within the scope of the appended claims and the equivalents thereof.

TABLE I

Viability Index

| Kidney # | ID# | O2/CO2/pH | Perfusion | Oxidative Index | Platelet Adherence | Viability Index | Outcome | |
|---|---|---|---|---|---|---|---|---|
| 1 | 9D12 | 0.063 | 1 | 1.05 | 0.75 | 2.86 | ATN, Peak Creatinine 3.3 mg/dL, Normal D9 | |
| 2 | 9D22 | 0.068 | 1 | 1.07 | 0.50 | 2.64 | ATN, Peak Creatinine 3.5 mg/dL, Normal D6 | MILD ATN |
| 3 | 9D07 | 0.060 | 1 | 1.00 | 0.50 | 2.56 | ATN, Peak Creatinine 3.7 mg/dL, Normal D7 | mean peak cr = 3.5 mg/dL |
| 4 | 9D11* | N.T. | 1 | 1.15 | N.T. | — | ATN, Peak Creatinine 6.9 mg/dL, Normal D17 | |
| 5 | 9D09 | 0.058 | 1 | 0.75 | 0.50 | 2.31 | ATN, Peak Creatinine 4.6 mg/dL, Normal D11 | |
| 6 | 21538 | 0.056 | 1 | 0.76 | 0.50 | 2.32 | ATN, Peak Creatinine 5.0 mg/dL, Normal D8 | MODERATE ATN |
| 7 | 9D10 | 0.041 | 1 | 0.87 | 0.50 | 2.41 | ATN, Peak Creatinine 6.0 mg/dL, Normal D10 | mean peak cr = 5.6 mg/dL |
| 8 | 9D15 | 0.047 | 1 | 0.76 | 0.15 | 1.96 | ATN, Peak Creatinine 7.5 mg/dL, Normal D18 | SEVERE ATN |
| 9 | 21558 | 0.025 | 1 | 0.33 | 0.25 | 1.61 | ATN, Peak Creatinine 13.0 mg/dL, Normal D20 | mean peak cr = 10.3 mg/dL |
| 10 | 21578 | 0.021 | −1 | 0.30 | 0.15 | −0.53 | PNF, euthanized D7 with creatinine 12.5 mg/dL | PNF |

*9D11 - kidney with missed double renal artery

What is claimed is:

1. A method for prospectively determining functional potential of an organ to be transplanted, said method comprising the steps of:
    (a) obtaining a value by measuring a parameter of a fluid derived from an explanted organ, said fluid selected from organ product, circulated perfusate, and a combination thereof;
    (b) comparing the value obtained from said measurement with a range of reference values indicative of normal organ function; and
    (c) determining whether or not said value falls within the range of reference values indicative of normal organ function.

2. A method for prospectively determining functional potential of an organ to be transplanted, wherein said organ is being perfused in a warm preservation system, said method comprising:
    (1) measuring at least one of the following parameters:
        (a) normalization of a perfusion characteristic for the organ;
        (b) extent of damage to the vascular endothelium of the organ;
        (c) level of oxidative capacity of the organ;
        (d) metabolic capacity of the organ; and
        (e) an organ-specific parameter of organ metabolism and function;
    (2) comparing the value obtained from said measurement with a range of reference values indicative of normal organ function; and
    (3) determining whether or not said value falls within the range of reference values indicative of normal organ function.

3. The method of claim 2, wherein a perfusion characteristic is chosen from vascular pressure and vascular flow rate.

4. The method of claim 2, wherein the organ is selected from the group consisting of kidney, heart, liver, small bowel, pancreas, lung, and eye.

5. The method of claim 4 further comprising the step of calculating a viability index wherein a value is assigned to each of the parameters evaluated, and wherein said viability index is the sum of said values and is indicative of how the kidney will function once it is transplanted.

6. The method of claim 2, wherein said organ is a kidney, and the organ-specific parameter is chosen from:
    (a) extent of leakage of a perfusate protein into urine produced by said kidney;
    (b) ability of said kidney to reabsorb ions;
    (c) ability of said kidney to secrete ions; and
    (d) ability of the kidney to retain a tracer molecule.

7. The method of claim 6, wherein said tracer molecule is an intracellular enzyme.

8. The method of claim 6, wherein said tracer molecule is a molecule having a molecular weight in the range of 30,000–180,000 daltons.

9. The method of claim 6, wherein said tracer molecule is chosen from perfluorochemical emulsion, dextran, inulin, immunoglobulin, and albumin.

10. The method of claim 2 wherein said organ is a liver, and the organ specific parameter is chosen from:
    (a) rate of bile flow from the liver;
    (b) concentration of liver enzymes in bile produced by the organ;
    (c) concentration of bile salts;
    (d) osmolarity of bile;
    (e) bile pH; and
    (f) bile color.

11. The method of claim 2 wherein said organ is a pancreas, and the organ-specific parameter is chosen from:
    (a) exocrine production by the pancreas;
    (b) exocrine concentration;
    (c) amylase activity of the pancreas;
    (d) lipase activity of the pancreas; and
    (e) insulin production by the pancreas.

12. The method of claim 2 wherein said organ is a heart, and the organ-specific parameter is chosen from:
    (a) mechanical activity of the heart;
    (b) electrical activity of the heart;
    (c) production of heart enzymes.

13. The method of claim 2 wherein said organ is a small bowel, and the organ-specific parameter is chosen from:
    (a) production of gastric secretions from the small bowel;
    (b) concentration of gastric secretions from the small bowel;
    (c) pH of gastric secretions from the small bowel; and
    (d) ability of the small bowel to absorb tracer molecules.

14. The method of claim 2 further comprising the step of calculating a viability index wherein a value is assigned to each of the parameters evaluated, and wherein said viability index is the sum of said values and is indicative of how the organ will function once it is transplanted.

15. The method of claim 2 wherein the extent of damage to the vascular endothelium of the organ is determined by assessing the degree of platelet adherence in the organ.

16. The method of claim 2 wherein the extent of damage to the vascular endothelium of the organ is determined by assessing the degree of platelet release from the organ.

17. The method of claim 2 wherein the extent of damage to the vascular endothelium of the organ is determined by assessing the degree of platelet activation in the organ.

18. The method of claim 2 wherein the level of oxidative capacity of the organ is determined by comparing an initial oxygen consumption value for said organ with a stabilized consumption value for said organ.

19. A method for determining the severity of ischemic damage to an organ intended for transplant, wherein said organ is being perfused in a warm preservation system, said method comprising:
   (1) measuring at least one of the following parameters:
      (a) normalization of a perfusion characteristic for the organ;
      (b) extent of damage to the vascular endothelium of the organ;
      (c) level of oxidative capacity of the organ;
      (d) metabolic capacity of the organ; and
      (e) an organ-specific parameter of organ metabolism and function;
   (2) comparing the value obtained from said measurement with a range of reference values indicative of normal organ function; and
   (3) determining whether or not said value falls within the range of reference values indicative of normal organ function.

20. The method of claim 19 further comprising the step of calculating a viability index wherein a value is assigned to each of the parameters evaluated, and wherein said viability index is the sum of said values and is indicative of the severity of ischemic damage to an organ intended for transplant.

21. A method for determining the severity of acute tubular necrosis of a kidney intended for transplant, wherein said kidney is being perfused in a warm preservation system, said method comprising:
   (1) measuring at least one of the following parameters:
      (a) normalization of a perfusion characteristic for the kidney;
      (b) extent of damage to the vascular endothelium of the kidney;
      (c) level of oxidative capacity of the kidney;
      (d) metabolic capacity of the kidney; and
      (e) an organ-specific parameter of organ metabolism and function;
   (2) comparing the value obtained from said measurement with a range of reference values indicative of normal kidney function; and
   (3) determining whether or not said value falls within the range of reference values indicative of normal kidney function.

22. The method of claim 21 further comprising the step of calculating a viability index wherein a value is assigned to each of the parameters evaluated, and wherein said viability index is the sum of said values and is indicative of the severity of acute tubular necrosis of the kidney intended for transplant.

23. A method for determining the extent of damage to vascular endothelium of a transplantable organ comprising:
   (1) determining at least one of the following parameters:
      (a) degree of platelet adherence to the vascular tissue of the organ;
      (b) degree of platelet release from the vascular tissue of the organ; and
      (c) degree of platelet activation in the organ;
   (2) determining the normal values for said parameter; and
   (3) comparing values from step (1) and values from step (2).

24. A method for prospectively identifying primary non-function (PNF) in an organ intended for transplant, wherein said organ is being perfused in a warm preservation system, said method comprising:
   (1) measuring at least one of the following parameters:
      (a) normalization of a perfusion characteristic for the organ;
      (b) extent of damage to the vascular endothelium of the organ;
      (c) level of oxidative capacity of the organ; and
      (d) metabolic capacity of the organ;
   (2) comparing the value obtained from said measurement with a range of reference values indicative of normal organ function; and
   (3) determining whether or not said value falls within the range of reference values indicative of normal organ function.

25. The method of claim 24, wherein the organ is selected from the group consisting of kidney, heart, liver, small bowel, pancreas, lung, and eye.

26. The method of claim 24 further comprising the step of calculating a viability index wherein a value is assigned to each of the parameters evaluated, and wherein said viability index is the sum of said values and is indicative of PNF of the organ intended for transplant.

* * * * *